US005229007A

United States Patent [19]
Ellenberger et al.
[11] Patent Number: 5,229,007
[45] Date of Patent: Jul. 20, 1993
[54] SELECTIVE REMOVAL OF AFLATOXIN FROM AZADIRACHTIN CONTAINING COMPOSITIONS

[75] Inventors: William P. Ellenberger; Suzanne R. Ellenberger, both of Salem, Utah

[73] Assignee: AgriDyne Technologies, Inc., Salt Lake City, Utah

[21] Appl. No.: 870,294

[22] Filed: Apr. 17, 1992

[51] Int. Cl.$^5$ .............................................. B01D 15/08

[52] U.S. Cl. .................................... 210/690; 210/694

[58] Field of Search ................................ 210/690, 694

[56] References Cited

U.S. PATENT DOCUMENTS 4,055,674 10/1977 Yano et al. .......................... 210/694

4,943,434 7/1990 Lidert .............................. 424/195.1

FOREIGN PATENT DOCUMENTS 2627613 12/1977 Fed. Rep. of Germany .

OTHER PUBLICATIONS

Dalvi et al. (1984) Avian Dis. 28(1):61–69.

Dalvi et al. (1984) Poultr Sci. 63(3):485–491.

Ademoyero et al. (1983) Toxicol. Lett. 16(1–2):153–157.

Hatch et al. (1982) Am. J. Vet. Res. 43(4):644–648.

Frank et al. (1972) Deut. Apoth. –2tg. 112(22):838.

Decker and Corby (1980) Vet. Hum. Toxicol. 22(6):388–389.

*Primary Examiner*—Ivars Cintins

*Attorney, Agent, or Firm*—Greenlee and Winner

[57] ABSTRACT

A method for the selective removal of contaminants, including aflatoxin, from azadirachtin-containing materials comprising contacting said materials with a binding agent capable of selectively binding contaminants compared to azadirachtin.

19 Claims, No Drawings

SELECTIVE REMOVAL OF AFLATOXIN FROM AZADIRACHTIN CONTAINING COMPOSITIONS

BACKGROUND OF THE INVENTION

The present invention relates to a method for the selective removal of contaminants, including aflatoxins, from azadirachtin-containing materials. More particularly, this invention relates to a method of reducing the aflatoxin content of azadirachtin-containing materials through the selective binding of aflatoxin by charcoal. Charcoal is defined as a black form of carbon produced by partially burning wood, coal, lignin, bone or other organic matter in a kiln from which air is excluded. Some of the synonyms for charcoal include carbon, activated carbon, and activated charcoal. Charcoal may be prewashed with acid or base with or without subsequent neutralization and may be in powder, granular or pelletized forms.

Extracts of the neem (*Azadirachta indica*) and the chinaberry (*Melia azedarach*) trees have long been known to have insecticidal activity (Natural Pesticides from the Neem Tree, Proc. 1st Int'l Neem Conf., Rottach-Egern, 1980 (H. Schmutterer, et al. eds. 1982); Natural Pesticides from the Neem Tree and Other Tropical Plants, Proc. 2nd Int'l Neem Conf., Rauisch holzhausen, 1983 (H. Schmutterer and K.R.S. Asher eds. 1984); Natural Pesticides from the Neem Tree and Other Tropical Plants, Proc. 3rd Int'l Neem Conf., Nairobi, 1986 (H. Schmutterer and K.R.S. Asher eds. 1987)). These extracts have generated intense academic research interest including the isolation and identification of at least sixty different chemical entities from various parts of the neem tree (P. Jones, et al., "The Chemistry of the Neem Tree," in Phytochemical Pesticides, Vol. 1 (M. Jacobson ed., CRC Press, 1988).

The active ingredient of the neem and chinaberry extracts, azadirachtin, is a limonoid of the tetranortriterpenoid type. This compound has been shown to be a potent insect growth regulator and feeding deterrent (Yamasaki, R. B., et al. (1987) J. Agric. Food Chem. 35:467–471). Several synthetic analogs of azadirachtin have been prepared (Yamasaki, R. B., et al. (1987) suora); Ley, S. V., et al. (1989) Tetrahedron 45:5175) and organic synthesis of the molecule has been accomplished (Ley, S. V., et al. (1987) Tetrahedron Lett. 28:221; Brasca, M. G., et al. (1988) Tetrahedron Lett. 29:1853; Ley, S. V., et al. (1989) Tetrahedron 45:2143; Nishikimi, Y., et al. (1989) J. Org. Chem 54:3354). Due to the complexity of the azadirachtin molecule, however, the economic synthesis and commercialization of a synthetic product is highly unlikely and therefore any salable product will require extraction from an azadirachtin-containing plant source.

Recently, two companies have received approvals for the sale of azadirachtin-containing neem seed extracts in the United States. The importance and attractiveness of these and future azadirachtin-containing extracts is due to their natural source, broad spectrum of insecticidal activity (Rembold, H., et al. (1981) Naturforsch C: Biosci. 36:466–469), lack of insect resistance, nonmutagenicity (Jacobson, M., Natural Pesticides from the Neem Tree, Proc. 1st Int'l Neem Conf., supra, pp. 33–42), and low mammalian toxicity (Nakanishi, K. (1975) Rec. Adv. Phytochem. 9:283–298).

Although the extraction of azadirachtin from plants and seeds has both economic and ecological advantages over organic synthesis, these extracts have the disadvantage of being easily susceptible to contamination with aflatoxins. These mycotoxins, produced by the fungi *Aspergillus flavus* and *Aspergillus parasiticus*, are known for their severe acute toxicity and potent carcinogenicity (Sargeant, et al. (1961) Nature 192:1096). Aflatoxin contamination is common in many agricultural commodities (e.g., corn, groundnuts, milk, dried chili peppers, cottonseed meal, coconut oil), including neem products, due to the growth of the fungi before and after harvesting and processing. During the extraction of azadirachtin from plants and seeds, aflatoxins are extracted and concentrated along with the desired compounds, specifically azadirachtin. Without removal, these aflatoxins could present serious health threats to the handlers and users of azadirachtin-containing extracts. Consequently, the presence of high levels of aflatoxin in commercial plant extracts render the material unacceptable to the producer and user because of health concerns.

Various methods of reducing the aflatoxin content of edible oils using physical and chemical techniques have been proposed. In the physical decontamination methods, the decomposition of aflatoxin is generally accomplished by the use of dry heat (Mann, G. E., et al. (1967) J. Agr. Food Chem. 15:1090; Lee, L. S., et al. (1969) J. Agr. Food Chem. 17:451) or moist heat (Coomes, T. J., et al. (1966) Nature 209:406). Chemical decontamination methods involve the decomposition of aflatoxin using ammonia (Gardner, H. K., et al. (1971) J. Am. Oil Chem. Soc'y 48:70; Masri, M. S., et al., U.S. Pat. No. 3,429,709), sodium hypochlorite (Fischbach, H., et al. (1965) J. Assoc. Off. Agr. Chemists 48:28), chlorine gas (Goldblatt, L. A. (1965) Abst. Meeting Am. Chem. Soc'y, 150th, p. 5a), hydrogen peroxide (Sreenivasamurthy, V., et al. (1967) J. Ass. Off. Anal. Chem. 50:350), methyl amine (Godfrey, E., et al., U.S. Pat. No. 3,585,041), liquid dimethyl ether and water (Yano, N., et al., U.S. Pat. No. 4,055,674), alkaline and acid solutions (Watanabe, H., et al., U.S. Pat. No. 4,280,962), mixtures of acetone, hexane and water (Goldblatt, L. A., et al., U.S. Pat. No. 3,515,736), and mixtures of an alkali or alkaline earth metal and an organic amine (Brandt, J., et al., U.S. Pat. No. 3,890,452). All of these methods degrade aflatoxin quite efficiently, but they have the inherent disadvantage of also degrading azadirachtin. These methods are therefore commercially impractical for the purification of azadirachtin-containing materials.

Methods of detoxication of aflatoxin-contaminated edibles using microbiological and adsorptive techniques have also been proposed. It has been reported, for example, that the nonpathogenic bacterium, *Flavobacterium aurantiacum*, somehow inactivates or removes aflatoxins from contaminated agricultural products (Ceigler, A. (1966) Appl. Microbiol. 14:934; Ceigler, A., et al., U.S. Pat. No. 3,428,458). Adsorptive methods for aflatoxin removal include the use of microbial mycelium (Masimango, N., et al. (1978) Eur. J. Appl. Microbiol. Biotechnology 6:101; Masimango, N., et al. (1979) Ann. Nutr. Aliment. 33:149), swollen clays (Masimango, N., et al. (1979) Ann. Nutr. Aliment. 33:137), and coconut wastes (Kumari, C. K., et al. (1987) Res. & Indus. 32:85). It is significant to note that these prior art methods all involve prolonged, costly and/or inefficient procedures and, like the chemical and physical detoxication methods, are commercially impractical for the treatment of extracts containing azadirachtin.

German Offen. No. 2,627,613 discloses the purification of a protein extract from oil seeds by treating it with activated carbon. The protein extract is reportedly deodorized and decontaminated by passing the extract through alkaline-pretreated activated carbon, eluting with alkaline solution, and treating the effluent with acid solution. Like the chemical treatments previously mentioned, this method is impractical for the purification of azadirachtin-containing compositions since azadirachtin, like aflatoxin, is degraded in alkaline solutions.

Administration of activated charcoal reportedly reduces the effects of aflatoxicosis in chickens. Dalvi, R., et al. (1984) Avian Dis. 28(1):61–69; Dalvi, R., et al. (1984) Poult. Sci. 63(3):485–491; Ademoyero, A., et al. (1983) Toxicol. Lett. 16(1-2):153–157. Similarly, goats afflicted with acute aflatoxicosis reportedly respond to treatment with activated charcoal or dual combinations of oxytetracycline or stanozolol and activated charcoal. Hatch, R. C., et al. (1982) Am. J. Vet. Res. 43(4):644–648. The removal of aflatoxin from aqueous solutions of the sugar xylitol by the use of charcoal has been demonstrated. Frank, P., (1972) Deut. Apoth. −2tg. 112(22):838. Although these references teach the reversal of aflatoxicosis and the absorption of aflatoxin from aqueous sugar solutions, none teach the selective removal of aflatoxin from organic or mixed organic-/aqueous solutions in the presence of azadirachtin.

A need therefore exists for a neem extract purification process which effectively and selectively removes aflatoxin, without concomitantly affecting azadirachtin content, and is practical and economical in operation.

SUMMARY OF THE INVENTION

In accordance with the present invention there is provided a practical and efficient method of removing aflatoxin from azadirachtin-containing extracts. Essentially, the aflatoxin decontamination in accordance with the invention is carried out by contacting the contaminated extract with an appropriate binding agent, preferably charcoal.

Another principal object of the invention is to provide a method for selectively removing aflatoxin from azadirachtin-containing extracts without affecting the azadirachtin content of said extracts. The primary advantages of the present invention are therefore its effectiveness and unexpected selectivity in removing aflatoxin, without concurrently removing or degrading azadirachtin.

Extracts decontaminated with charcoal in accordance with the invention have the contaminating aflatoxin removed or reduced to a low level which renders the azadirachtin-containing extract suitable for processing and use, particularly for use as an insecticidal agent.

The need for heat and chemical treating agents previously employed for edible oils is avoided. The active ingredient of the plant extract, azadirachtin, is not adversely affected by the physical and chemical processing.

Finally, the procedure is simple, expedient, and can be carried out in a variety of readily-available solvents. The solvent is readily evaporated under vacuum.

DESCRIPTION OF THE PREFERRED EMBODIMENTS

The invention relates to a method for the selective removal of aflatoxin from azadirachtin-containing compositions. The invention is characterized by dissolving or suspending said compositions in solvent and placing these solutions in contact with charcoal. The charcoal can be in granular, powdered or pelletized form and the method of contact can be as a stirred mixture, drum, filter or column device, or by any like method known in the art.

Aflatoxin removal in accordance with the process of the present invention is effective with agricultural products in general and particularly applicable to azadirachtin-containing agricultural products. Neem seed extracts are particularly of interest and provide an illustrative embodiment which is preferred for charcoal binding.

As used herein, "selective removal" means the relative proportion of aflatoxin to azadirachtin is substantially decreased after treatment. In the examples shown, the percent loss of aflatoxin is substantially greater than the percent loss of azadirachtin. "Substantially all," as used herein, means at least 90% of the contaminating aflatoxin was bound and removed following treatment.

As briefly noted above, the elimination of aflatoxin is accomplished by contacting the contaminated material with charcoal. In general, the process comprises the following steps: (a) admixing the aflatoxin-contaminated composition with a sufficient amount of solvent, preferably ethyl acetate, to result in a flowable mixture; (b) contacting said mixture with charcoal, preferably by stirring the mixture with powdered charcoal or passing the mixture through granular charcoal; (c) removing particulate charcoal by filtration; and (d) evaporating the solvent to recover the purified azadirachtin-containing material.

The preferred binding agent in this process, charcoal, is advantageous due to the fact that charcoal does not bind substantial amounts of azadirachtin, and because numerous impurities are removed from the crude composition in addition to aflatoxin. The method is useful for removing contaminants from an azadirachtin-containing composition by virtue of the aforesaid surprising properties. Charcoal is widely available in commerce from several manufacturers, and is produced in various brands, grades and forms. Any form or grade of charcoal is suitable.

It has been found that a wide variety of other solvents, in addition to ethyl acetate, may be used with good results. Any solvent or combination of solvents which solubilizes or suspends azadirachtin without causing the decomposition of azadirachtin is suitable. It has been discovered, however, that the efficiency with which aflatoxin is absorbed depends, at least in part, on the particular solvent(s) selected. Suitable solvents for use in this invention include, but are not limited to, acetone, dichloromethane, ethanol, ethyl acetate, ethylene dichloride, methanol, methyl acetate, methyl t-butyl ether, methyl formate and 2-propanol. Preferred solvents are ethyl acetate, methyl acetate, methyl formate and acetone. Most preferably, the solvent is ethyl acetate. These solvents are also relatively inexpensive and readily available.

The ratio by weight of azadirachtin-containing material to charcoal is not critical, but does affect the rate and efficiency of aflatoxin removal. Generally, it has been found that good results are obtained when a ratio of two parts azadirachtin-containing material to one part (or greater) charcoal is used. The contact time between the azadirachtin-containing material and the charcoal is generally increased as the percentage of charcoal is decreased. However, there is not a critical contact time.

The treatment is independent of the temperature of the process. It is well known, however, that azadirachtin decomposes at elevated temperatures. Therefore, the preferred operating temperature is 20°-25° C. The evaporation of solvent is performed under reduced pressures thus allowing relatively low temperatures and/or short contact times to be utilized.

The aflatoxin concentration in azadirachtin-containing materials is measured by high performance liquid chromatography (HPLC). The sample must first be prepared for analysis by immunoaffinity column cleanup, followed by derivatization of the aflatoxins with trifluoroacetic acid (TFA), and determination of the derivatives with HPLC combined with fluorescence detection. See Tarter, E. J., et al. (1984) J. Assoc. Off. Anal. Chem. 67:597; Park, D. L., et al. (1990) J. Assoc. Off. Anal. Chem. 73:260; Trucksess, M. W., et al. (1991) J. Assoc. Off. Anal. Chem. 74:81; AOAC Official Methods of Analysis 1184-1283 (15th Ed., K. Helrich ed., 1990), Aflatest TM Mycotoxin Testing System User's Guide from Vicam L. P., 29 Mystic Avenue, Somerville, Mass. 02145. The dichromate standard and calibration of UV Spectrophotometers is based on AOAC Official Method 970.44. The standardization of aflatoxin solutions is based on AOAC Official Methods 971.22.

The analysis of azadirachtin content in azadirachtin-containing materials is determined by HPLC using an external, analytically pure azadirachtin standard curve. Representative examples of this type of method from the literature include Uebel, E. C., et al. (1979) "C-18 HPLC," J. Liq. Chromatography 2:875; Warthen, J. D. Jr., et al. (1984) J. Liq. Chromatography 7:591; Yamasaki, R. B., et al. (1986) "Phenyl HPLC," J. Chromatography 356:220; and Huang, H. and Morgan, E.D. (1990) "Supercritical Fluid Chromatography," J. Chromatography 519:137.

The process of the invention will become more clear from consideration of the following examples which are set forth to further illustrate the process of the invention and are not intended, in any way, to be limitative thereof.

EXAMPLES

Example 1

Treatment of Aflatoxin-Contaminated Neem Seed Extract Using Powdered Charcoal and Ethyl Acetate Neem seed extract (20.5 grams) contaminated with 2920 ppb of aflatoxin ($B_1$) was added to 20.6 grams of powdered charcoal (Norit A) and 210 mL of ethyl acetate. The aflatoxin binding was carried out at room temperature for 16 hours with stirring. After completion of the binding, the neem extract and solvent were separated from the spent charcoal by filtration through a bed of diatomaceous earth. The filter cake comprising impurities, including the aflatoxin-bound charcoal, was washed with 100 mL of ethyl acetate. The ethyl acetate solvent was then removed under vacuum at 40° C. Measurement of aflatoxin was by means of a modified AOAC Official Method, i.e., immunoaffinity column, HPLC and fluorescence analysis, described in current publications (see, for instance, Tarter, E. J., et al. (1984) J. Assoc. Off. Anal. Chem. 67:597; Park, D. L., et al. (1990) J. Assoc. Off. Anal. Chem. 73:260; Trucksess, M. W., et al. (1991) J. Assoc. Off. Anal. Chem. 74:81; AOAC Official Methods of Analysis 1184-1283 (15th Ed., K. Helrich ed., 1990), Aflatest TM Mycotoxin Testing Stystem User's Guide from Vicam L. P., 29 Mystic Avenue, Somerville, Mass. 02145). Analysis of azadirachtin was by HPLC using an external, analytically pure azadirachtin standard curve as described in, for instance, Uebel, E. C., et al. (1979) "C-18 HPLC," J. Liq. Chromatography 2:875; Warthen, J. D. Jr., et al. (1984) J. Liq. Chromatography 7:591; Yamasaki, R. B., et al. (1986) "Phenyl HPLC," J. Chromatography 356:220; and Huang, H. and Morgan, E.D. (1990) "Supercritical Fluid Chromatography," J. Chromatoqraphy 519:137. The results of the analyses for aflatoxin and azadirachtin content are shown in Table 1. It can be seen that substantial amounts of impurities other than aflatoxin were also removed.

TABLE 1

Results of purification of neem seed extract contaminated with 2920 ppb of alfatoxin with powdered charcoal (Norit A) and ethyl acetate

|  | Initial | Treated |
| --- | --- | --- |
| Gross weight | 20.5 g | 18.2 g |
| Percent azadirachtin | 13.7% | 15.8% |
| Weight azadirachtin | 2.81 g | 2.87 g |
| Percent loss azadirachtin | — | <1% |
| ppb aflatoxin $B_1$ | 2920 ppb | 10 ppb |
| Percent loss aflatoxin $B_1$ | — | >99% |

Example 2

Treatment of Aflatoxin-Contaminated Neem Seed Extracts Using Various Solvents

The same procedures were followed as in Example 1 above except that different solvents were employed. The treated and untreated neem seed extracts were analyzed for aflatoxin and azadirachtin content. The results of the comparative azadirachtin evaluation are set out in the table of values below. It can be seen that a wide variety of solvents may be used with good results.

TABLE 2

Comparative Evaluation of Various Solvents on Selective Removal of Aflatoxin From Neem Seed Extracts

|  | Percent Loss Azadirachtin | Percent Loss Aflatoxin $B_1$ | Final Content Aflatoxin $B_1$ |
| --- | --- | --- | --- |
| Acetone | <1% | >99% | 19 ppb |
| Benzene | 4% | >99% | 29 ppb |
| Dichloromethane | 4% | >98% | 49 ppb |
| Ethanol | 8% | >99% | 15 ppb |
| Ethyl Acetate | <1% | >99% | 10 ppb |
| Ethylene Dichloride | <1% | >98% | 53 ppb |
| Methanol | 8% | >99% | 15 ppb |
| Methyl Acetate | <1% | >99% | 17 ppb |
| Methyl t-Butyl Ether | 9% | >99% | 22 ppb |
| Methyl Formate | <1% | >99% | 19 ppb |
| 2-Propanol | 6% | >99% | 15 ppb |

Example 3

Treatment of Aflatoxin-Contaminated Neem Seed Extracts Using Various Powdered Charcoals The same procedures were followed as in Example 1 above except that different types of powdered charcoal were employed, and the weight of charcoal was 50% that of the initial neem seed extract. The treated and untreated neem seed extracts were analyzed for aflatoxin and azadirachtin content. The results of the comparative evaluation are set out in the table of values below. It can be seen that any brand or grade of powdered charcoal is suitable.

TABLE 3

Comparative Evaluation of Various Powdered Charcoals on Selective Removal of Aflatoxin From Neem Seed Extracts

| | Percent Loss Azadirachtin | Percent Loss Aflatoxin $B_1$ | Final Content Aflatoxin $B_1$ |
|---|---|---|---|
| Norit A | 1% | >99% | <1 ppb |
| Darco KB | 14% | >99% | 13 ppb |
| Darco KBB | 3% | >99% | 12 ppb |
| Norit USP | <1% | >99% | 13 ppb |
| Darco G-60 | 9% | >99% | 20 ppb |
| Darco S51 | <1% | >98% | 44 ppb |
| Sigma C-5260 | 1% | >99% | <1 ppb |
| Sigma C-5385 | 1% | >99% | 3 ppb |

Example 4

Effect of Charcoal Loading and Stir Time on the Selective Removal of Aflatoxin from Neem Seed Extracts The same procedures were followed as in Example 1 above except for the amount of charcoal added and the stir times employed. The treated and untreated neem seed extracts were analyzed for aflatoxin and azadirachtin content. The results of the comparative evaluation are set out in the table of values below. Charcoal load is expressed as the weight percent of the azadirachtin-containing extract. Stir times are as listed.

TABLE 4

Effect of Adsorbent Concentration and Stir Time on the Selective Removal of Aflatoxin from Neem Seed Extracts

| Charcoal Load | | Percent Loss Azadirachtin | Percent Loss Aflatoxin $B_1$ | Final Content Aflatoxin $B_1$ |
|---|---|---|---|---|
| 100% | 2 hr | 3% | >99% | 9 ppb |
| | 4 hr | <1% | >99% | 7 ppb |
| | 6 hr | 3% | >99% | 8 ppb |
| | 16 hr | 1% | >99% | 7 ppb |
| 50% | 2 hr | 4% | >99% | 18 ppb |
| | 4 hr | 3% | >99% | 15 ppb |
| | 6 hr | 3% | >99% | 17 ppb |
| | 16 hr | 4% | >99% | 15 ppb |
| 25% | 2 hr | 2% | >94% | 118 ppb |
| | 4 hr | 3% | >95% | 100 ppb |
| | 6 hr | 2% | >95% | 101 ppb |
| | 16 hr | 1% | >96% | 63 ppb |
| 10% | 2 hr | 1% | >90% | 205 ppb |
| | 4 hr | 3% | >89% | 215 ppb |
| | 6 hr | <1% | >90% | 188 ppb |
| | 16 hr | 1% | >90% | 190 ppb |

Example 5

Treatment of Aflatoxin-Contaminated Neem Seed Extract With Varying Solvent Volume The same procedures were followed as in Example 1 above except that the solvent volume was varied. The weight of neem seed extract in each sample was 20 grams. The results of the analysis of aflatoxin and azadirachtin content are shown in Table 5. It can be seen that solvent concentration has a negligible effect on the selective removal of aflatoxin from neem seed extracts.

TABLE 5

Effect of Solvent Concentration on the Selective Removal of Aflatoxin from Neem Seed Extracts

| | Percent Loss Azadirachtin | Percent Loss Aflatoxin $B_1$ | Final Content Aflatoxin $B_1$ |
|---|---|---|---|
| 50 mL | 5% | >99% | 7 ppb |
| 75 mL | 5% | >99% | 8 ppb |
| 100 mL | 6% | >99% | 8 ppb |
| 200 mL | 4% | >99% | 12 ppb |
| 300 mL | 8% | >99% | 10 ppb |

Example 6

Treatment of Aflatoxin-Contaminated Neem Seed Extract With Varying Solvent Temperature The same procedures were followed as in Example 1 above except that the solvent temperature was varied. As Table 6 illustrates, solvent temperature has a negligible effect on the selective removal of aflatoxin from neem seed extracts.

TABLE 6

Effect of Solvent Temperature on the Selective Removal of Aflatoxin from Neem Seed Extracts

| | Percent Loss Azadirachtin | Percent Loss Aflatoxin $B_1$ | Final Content Aflatoxin $B_1$ |
|---|---|---|---|
| 0° C. | 3% | >99% | 12 ppb |
| 20–25° C. | 4% | >99% | 12 ppb |
| 40–45° C. | 4% | >99% | 8 ppb |
| 78° C. | 5% | >99% | 5 ppb |

Example 7

Treatment of Aflatoxin-Contaminated Neem Seed Extract Using Granular Charcoal and Ethyl Acetate Neem seed extract (22.0 grams) was mixed with 220 mL of ethyl acetate. Aflatoxin was removed by passing the mixture through a column of granular carbon (Norit PK 0, 25-1; 22.0 grams). The treatment was further repeated four times. After completion of the five treatments, the carbon column was rinsed with 100 mL of ethyl acetate. The ethyl acetate solvent was then removed under vacuum at 40° C. The treated and untreated neem seed extracts were analyzed for aflatoxin and azadirachtin content as described in Example 1. The results of the analyses are shown in Table 7. It can be seen that substantial amounts of impurities other than aflatoxin were also removed.

TABLE 7

Results of Purification of Neem Seed Extract With Granular Carbon and Ethyl Acetate

| | Initial | Treated |
|---|---|---|
| Gross Weight | 22.0 g | 20.2 g |
| Percent Azadirachtin | 13.7% | 14.5% |
| Weight Azadirachtin | 3.01 g | 2.93 g |
| Percent Loss Azadirachtin | | 3% |
| ppb Aflatoxin $B_1$ | 2920 ppb | 22 ppb |
| Percent Loss Aflatoxin $B_1$ | | >99% |

Example 8

Treatment of Aflatoxin-Contaminated Neem Seed Extracts Using Various Granular Charcoals The same procedures were followed as in Example 8 above except that different granular charcoals were employed. The results of the comparative evaluation are set out in the table of values below.

TABLE 8

Comparative Evaluation of Various Granular Charcoals on Selective Removal of Aflatoxin From Neem Seed Extracts

|  | Percent Loss Azadirachtin | Percent Loss Aflatoxin $B_1$ | Final Content Aflatoxin $B_1$ |
| --- | --- | --- | --- |
| Norit PK 0 | 3% | >99% | 22 ppb |
| Darco 12 × 40 | 11% | >98% | 60 ppb |
| Norit C | 18% | >98% | 58 ppb |

What we claim is:

1. A method for the selective removal of aflatoxin from an azadirachtin-containing composition contaminated therewith which comprises contacting said azadirachtin-containing composition with activated carbon, whereby said activated carbon selectively binds aflatoxin compared to azadirachtin.

2. A method according to claim 1 wherein the activated carbon is charcoal.

3. A method according to claim 1 wherein the activated carbon is added in an amount and for a time sufficient to remove substantially all of said aflatoxin from said azadirachtin-containing composition.

4. A method according to claim 1 wherein said contacting is accomplished by making a flowable mixture of said azadirachtin-containing composition in a solvent which is non-degrading to azadirachtin, and subjecting said mixture to activated carbon.

5. A method according to claim 4 wherein the solvent is selected from the group consisting of nitriles, substituted aromatics, chlorinated aliphatics, aromatic aldehydes, sulfones, ethers, esters, amides, sulfoxides, alcohols, alkyl carbonates, ketones, and mixtures thereof.

6. A method according to claim 4 wherein the solvent is selected from the group consisting of acetone, benzene, dichloromethane, ethanol, ethyl acetate, ethylene dichloride, methanol, methyl acetate, methyl t-butyl ether, methyl formate, 2-propanol, and mixtures thereof.

7. A method according to claim 1 wherein the azadirachtin-containing composition is a neem seed extract.

8. A method according to claim 1 wherein the selective removal of aflatoxin is carried out in a succession of treatments.

9. A method for the selective removal of aflatoxin from an azadirachtin-containing composition contaminated therewith which comprises the steps of:
   (a) mixing said azadirachtin-containing composition with an azadirachtin-soluble solvent and activated carbon for a time sufficient to bind aflatoxin, wherein said solvent is non-degrading to azadirachtin, and whereby aflatoxin is selectively bound to said activated carbon; and
   (b) separating the activated carbon and bound aflatoxin from the azadirachtin-containing composition.

10. A method according to claim 9 wherein the activated carbon is charcoal.

11. A method according to claim 9 wherein the solvent is selected from the group consisting of nitriles, substituted aromatics, chlorinated aliphatics, aromatic aldehydes, sulfones, ethers, esters, amides, sulfoxides, alcohols, alkyl carbonates, ketones, and mixtures thereof.

12. A method according to claim 9 wherein the solvent is selected from the group consisting of acetone, benzene, dichloromethane, ethanol, ethyl acetate, ethylene dichloride, methanol, methyl acetate, methyl t-butyl ether, methyl formate, 2-propanol, and mixtures thereof.

13. A method according to claim 9 wherein the activated carbon is added in an amount and for a time sufficient to bind substantially all of said aflatoxin from said azadirachtin-containing composition.

14. A method according to claim 9 wherein the solvent is ethyl acetate.

15. A method for the selective removal of aflatoxin from an azadirachtin-containing composition contaminated therewith which comprises the steps of:
   (a) admixing said azadirachtin-containing composition with a solvent which is non-degrading to azadirachtin, wherein a flowable mixture is formed; and
   (b) passing said mixture through a column of activated carbon wherein said activated carbon selectively binds aflatoxin compared to azadirachtin; and optionally
   (c) repeating step (b) to remove substantially all of said aflatoxin.

16. A method according to claim 15 wherein the activated carbon is charcoal.

17. A method according to claim 15 wherein the solvent is selected from the group consisting of nitriles, substituted aromatics, chlorinated aliphatics, aromatic aldehydes, sulfones, ethers, esters, amides, sulfoxides, alcohols, alkyl carbonates, ketones, and mixtures thereof.

18. A method according to claim 15 wherein the solvent is selected from the group consisting of acetone, benzene, dichloromethane, ethanol, ethyl acetate, ethylene dichloride, methanol, methyl acetate, methyl t-butyl ether, methyl formate, 2-propanol, and mixtures thereof.

19. A method according to claim 15 wherein the azadirachtin-containing composition is a neem seed extract.

* * * * *

UNITED STATES PATENT AND TRADEMARK OFFICE
CERTIFICATE OF CORRECTION

PATENT NO. : 5,229,007

DATED : July 20, 1993

INVENTOR(S) : Suzanne R. Ellenberger; William P. Ellenberger

It is certified that error appears in the above-identified patent and that said Letters Patent is hereby corrected as shown below:

On the cover page, item [75], the named inventors should be: Suzanne R. Ellenberger; William P. Ellenberger, both of Salem, Utah At column 1, line 44, "suora" should read --supra--.

At column 6, line 18, "Chromatoqra-" should read --Chromatogra- --.

Signed and Sealed this

Twelfth Day of April, 1994

Attest:

BRUCE LEHMAN

*Commissioner of Patents and Trademarks*

*Attesting Officer*